United States Patent [19]
Matz

[11] Patent Number: 6,135,974
[45] Date of Patent: Oct. 24, 2000

[54] POST-INJURY SUPPORT HOSE

[76] Inventor: Samuel O. Matz, 10 Woodgait Ct., Reistertown, Md. 21136

[21] Appl. No.: 09/046,746

[22] Filed: Mar. 24, 1998

[51] Int. Cl.[7] .......................... A61F 13/00; A41B 11/00; A41B 11/04

[52] U.S. Cl. ................ 602/62; 602/60; 602/63; 2/239; 2/409

[58] Field of Search ................ 2/239–242, 917, 2/919; 602/20, 21, 60, 61, 62, 63, 64; 128/878, 879, 881, 882

[56] References Cited

U.S. PATENT DOCUMENTS

| | | |
|---|---|---|
| 1,287,870 | 12/1918 | Burk . |
| 1,775,714 | 9/1930 | Bass . |
| 3,473,527 | 10/1969 | Spiro . |
| 3,605,122 | 9/1971 | Myers ........................................... 2/242 |
| 3,902,503 | 9/1975 | Gaylord, Jr. ............................. 128/559 |
| 3,975,929 | 8/1976 | Fregeolle .................................... 66/172 |
| 4,036,220 | 7/1977 | Bellasalma . |
| 4,176,665 | 12/1979 | Terening . |
| 4,198,834 | 4/1980 | Reid, Sr. .................................... 66/172 |
| 4,599,812 | 7/1986 | Harmsen .................................. 2/239 X |
| 5,020,523 | 6/1991 | Bodine . |
| 5,086,543 | 2/1992 | Mitchell ...................................... 24/16 |
| 5,139,476 | 8/1992 | Peters ......................................... 602/26 |
| 5,275,179 | 1/1994 | Lonardo ................................... 128/882 |
| 5,399,153 | 3/1995 | Caprio, Jr. et al. ....................... 602/26 |
| 5,413,957 | 5/1995 | Bradberry ................................. 602/63 |
| 5,425,701 | 6/1995 | Oster et al. ............................... 602/23 |

FOREIGN PATENT DOCUMENTS

| | | | |
|---|---|---|---|
| 2492656 | 4/1982 | France ...................................... 602/63 |
| 4230165 | 3/1994 | Germany .................................. 602/63 |
| 2111833 | 7/1983 | United Kingdom ..................... 602/63 |

OTHER PUBLICATIONS

Venosan Legline brochure; Updated—Admitted Prior Art.

*Primary Examiner*—Kim M. Lee
*Attorney, Agent, or Firm*—Rhodes & Mason, PLLC

[57] ABSTRACT

A compression hose having a extremity covering portion and an injured area covering portion. The injured area covering portion further includes an opening that is positioned over the patient's injured area. A number of fastening straps are fixedly attached to one side of the opening and are sized to extend across the opening and secured to a fastener receiver. A locking strap having a longer length than inner fastening straps is positioned at the outer edge of the hose and is sized to extend across the opening and lock the hose in place on the patient's extremity.

21 Claims, 3 Drawing Sheets

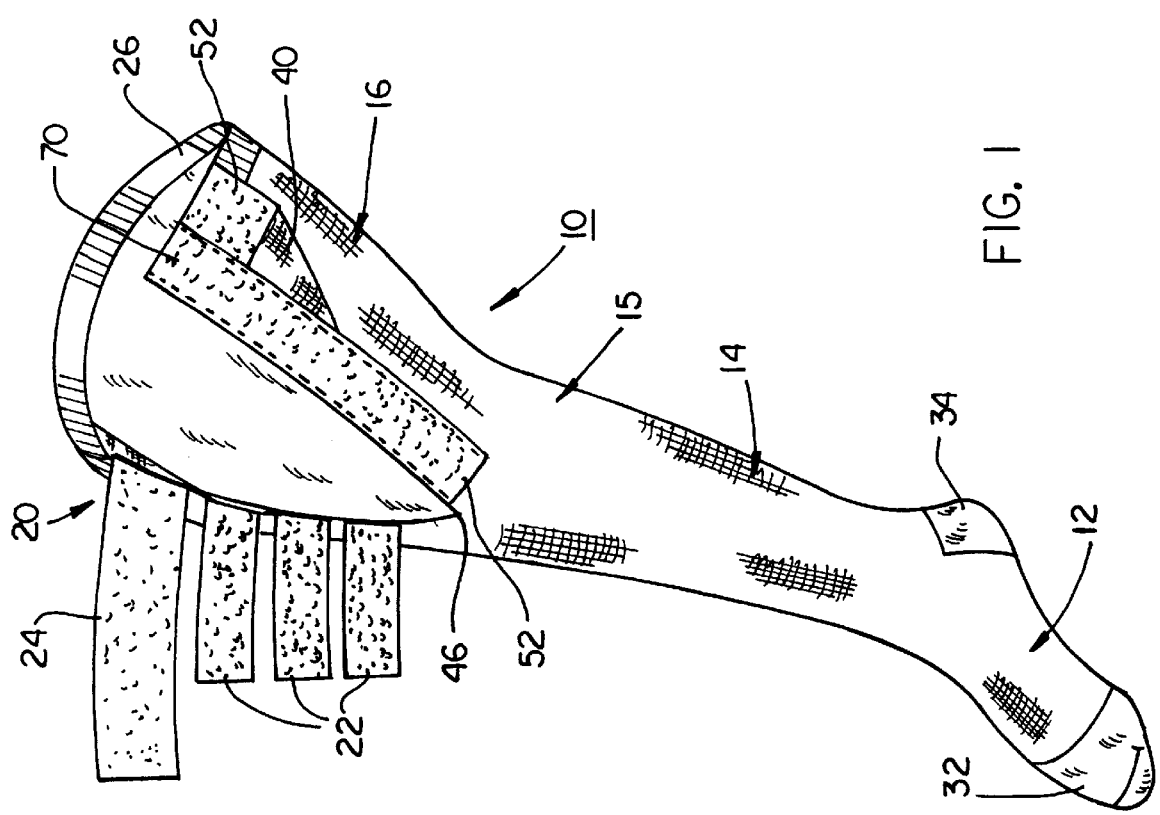
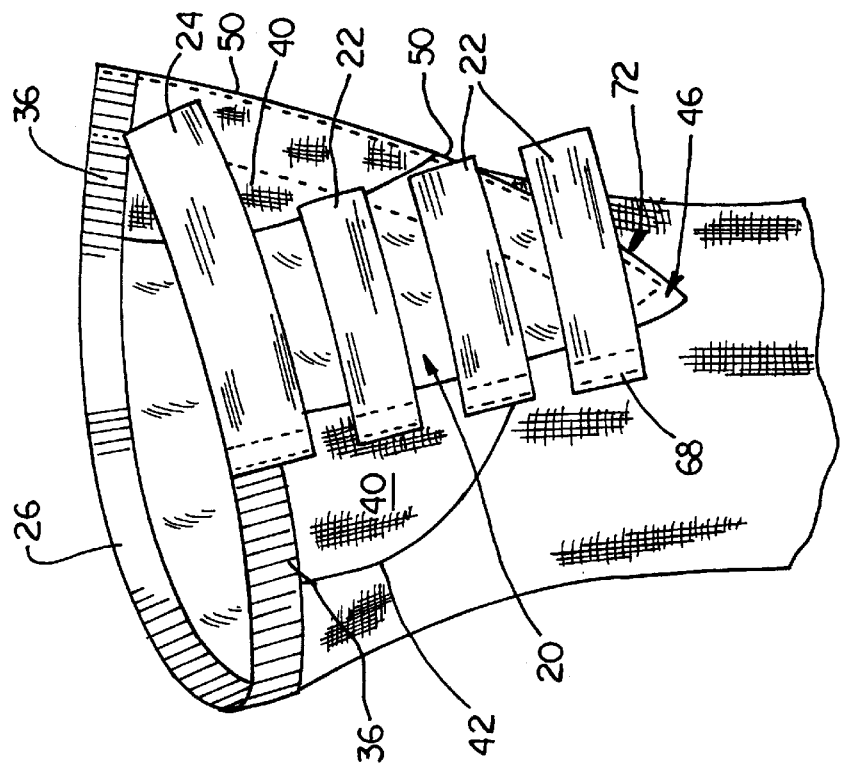
FIG. 1
FIG. 2

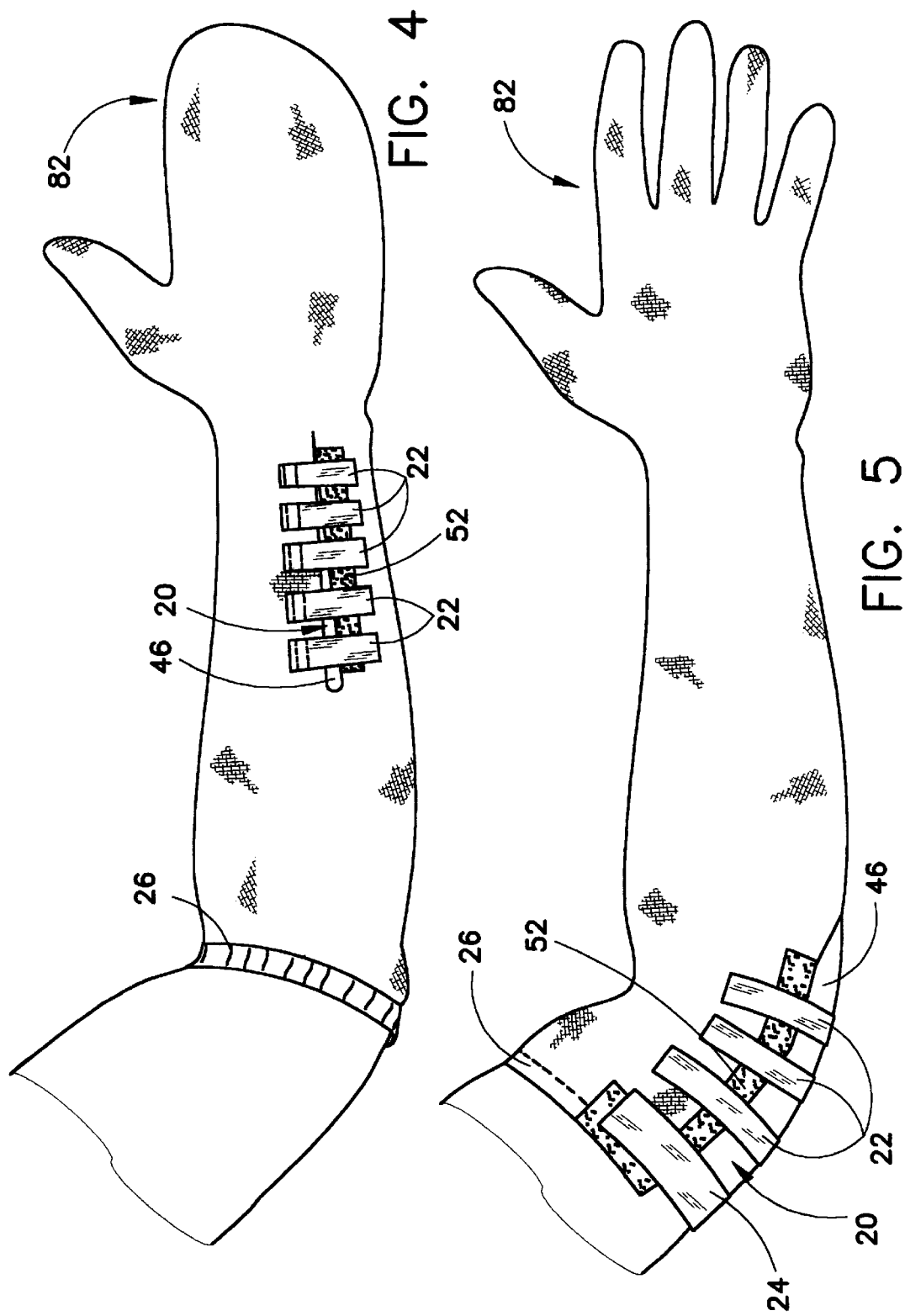

POST-INJURY SUPPORT HOSE

FIELD OF THE INVENTION

The present invention relates to post-injury support hose for patients who have sustained an injury to an extremity. More particularly, the present invention relates to a compression hose for improving circulation of the extremity having a front opening extending over the injured area with reclosable fasteners for attachment over the area without interfering with the injury or bandages.

BACKGROUND OF THE INVENTION

The present invention provides improvements in post-injury dressing for patients who have sustained an injury to an extremity. Numerous medical studies have proven that applying compression to an extremity is an important factor in reducing blood flow problems. Stockings and hosiery have been used to apply compression to the legs of patients who have recently undergone surgery to speed the blood flow and reduce blood clotting. The preferred hose apply a graduated compression with the highest compression rates in the foot and lower calf areas and reduced amounts of compression higher in the leg. Although these types of hose are advantageous, presently available hose have several drawbacks.

One presently available post-operative wrap is an elastic bandage such as an "ace-type wrap". These wraps effectively hold a dressing or sponge on the post-operative wound but do not apply compression throughout the entire lower leg area and may cause swelling of the foot and ankle. These types of bandages often have a limited size and do not extend below the upper calf when wrapped around the patient's leg. The bandage is held in position by metal clips which may cause puncture wounds to the patient if they are not carefully placed onto the bandage, or may fall off the bandage and become lost. Worse, this alignment may cause a "tourniquet effect" which reduces blood flow to the lower leg and exacerbates the potential complication of post-injury thrombophlebitis.

A drawback of conventional compression hose is that they do not provide access to the injured area. For example, after a patient has undergone arthroscopic surgery, the doctor will place the hose initially on the outer extremity and then pull the hose along the extremity. The injured area should be accessible to change bandages or allow a doctor to examine the area. Hosiery that extends over the area of injury does not allow for this convenience. Additionally, it is difficult to put the hosiery on and off without disturbing or displacing the bandages.

Thus, there exists a need for a compression type hose capable of applying graduated compression throughout the length of the extremity and having an opening over the injured area for accessing the patient's wound and dressing.

SUMMARY OF THE INVENTION

The present invention provides a post-injury support hose that has graduated compression rates along a patient's extremity and has an opening for accessing the injured area. The compression hose includes an extremity covering portion and an injured area covering portion. The injured area covering portion has an opening and reclosable fasteners to permit closure of the opening. A patient's extremity is inserted into the hose such that the opening is aligned with the injured area. Dressings on the patient's injured area may be applied or changed and the reclosable fasteners may be secured about the dressing to provide compression to the extremity around the injured area and prevent thrombophlebitis or other circulatory impairment.

Preferably, the medical compression hose has a graduated compression force which is greater in the distal area of the extremity and gradually decreases along the length of the hose further along the patient's extremity. One specific embodiment includes a hose for use on a patient's leg that places a compression rate above the patient's ankle in the range of about 15 to 20 mm/Hg. The compression rate gradually decreases to a rate in the range of about 8 to 14 mm/Hg at the patient's upper calf immediately below the knee.

The upper edge of the hose may include an elastic band for holding the hose in place on the patient's extremity. Reclosable fasteners may be securely attached by stitching to one side of the opening and are of sufficient length to extend across the opening and fasten to a fastener receiver positioned on the other side of the opening. Preferably, a locking strap positioned on the hose edge is longer than the other straps to lock the hose in position on the patient's extremity and prevent it from sliding down. The fastener straps may be positioned to accommodate a variety of compression rates throughout the extremity and injured area.

A panel may be attached to the hose adjacent to the opening to allow the hose to fit around the patient's extremity. The panel is connected to the hose by a seam located on the exterior of the hose away from the patient's skin. The panel may also include an upper edge that in combination with the elastic band and straps maintains the hose on the patient's extremity.

The present invention also includes a method of applying a compression hose to a patient. The method includes inserting the patient's extremity into the hose, pulling the hose onto the patient's extremity, positioning the opening over the injured area, and releasably fastening a number of straps across the opening. This method provides for the straps to be unfastened to allow access to the injured area for changing or inspecting bandages or other dressings. The hose applies a graduated compression force to the patient's extremity. The straps fasten across the opening and attach to fastener receivers on the opposite side of the opening.

BRIEF DESCRIPTION OF THE DRAWINGS

This invention will be better understood from the reading of the detailed description of the preferred embodiment along with a review of the drawings, wherein like items are indicated by the same reference number:

FIG. 1 is a side elevational view of a compression hose according to an embodiment of the invention with the fasteners in an open position;

FIG. 2 is an enlarged partial elevational view of a compression hose according to the present invention in which the fasteners are open;

FIG. 4 is a side elevational view of a hose having an opening placed over a patient's wrist; and FIG. 5 is a side elevational view of a hose having an opening over the patient's elbow.

DETAILED DESCRIPTION OF THE PREFERRED EMBODIMENT

Figure 3:
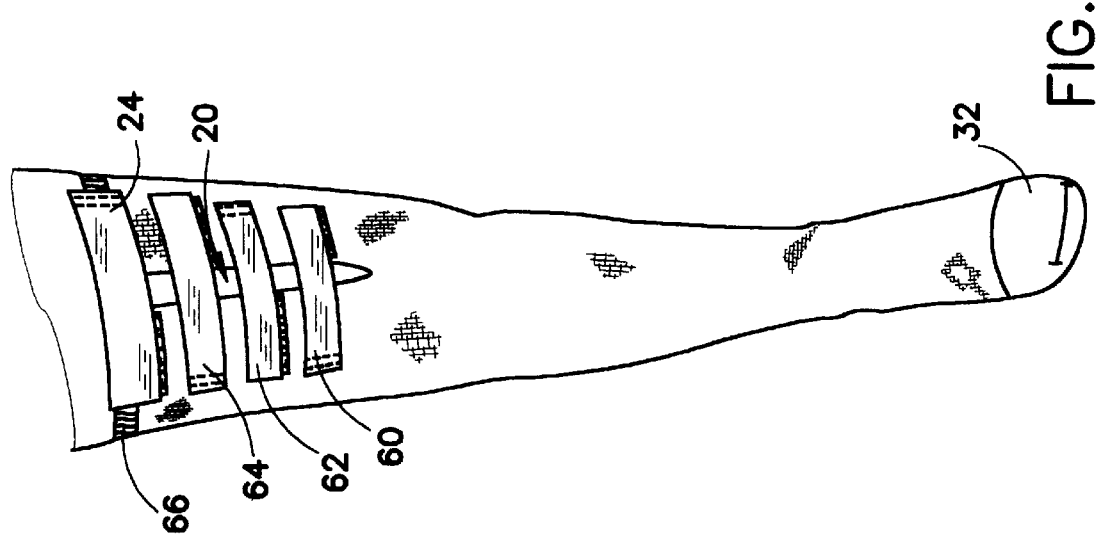
FIG. 3 is a front elevational view of a compression hose having straps that extend across the opening from opposite sides.

With reference to FIG. 1, the overall design of the preferred embodiment of the present compression hose is shown. It is understood that the present invention has applications to any number of different positions on the body, and the word extremity used herein is meant to refer to the patient's arm or leg. The terms proximal and distal are used to indicate relative positions along the extremity of the patient. Distal defines the area situated away from the central point of the patient's body and proximal defines the area nearer the central point of the body. By way of examples, a patient's wrist is distally located on the extremity relative the elbow, the elbow is distally located on the extremity relative to the shoulder. Conversely, the knee is proximally located on the leg relative to the ankle. Likewise, descriptions of the hose including inner end and upper end are used to define locations of the elements on the hose. For example, FIG. 1 illustrates an opening 20 located at the inner end of the hose, compared with FIG. 4 that illustrates an opening towards the outer end of the hose. The specific embodiments shown and discussed in the application are not meant to limit the invention, but rather are meant to explain the invention that includes having a compression hose to assist blood flow and an opening to access the injured area.

The term injured area is defined as the part of the patient's extremity that has a wound or has been surgically operated upon. For example, the wrist area is the injured area for a patient who has carpal tunnel syndrome in the wrist or has undergone arthroscopic surgery on the wrist. The present invention is not limited to only applications after surgery, but may be used at any time during the healing of an injury.

In one embodiment illustrated in FIG. 1, the invention provides a single hose 10 having a foot portion 12a, calf portion 14, an upper calf portion 15, and a thigh portion 16. As will be apparent, the need for this particular hose style exists only on the operated-on knee. The other leg occasionally receives a conventional medical compression stocking, unless, of course, surgery is performed on both knees, which is unusual.

An opening 20 extends from the upper calf portion to the top of the hose. One side of the opening 20 includes a number of fastening or locking straps 22, 24 fixedly attached to the hose 10 and sized to extend across the opening and secure to a fastener receiver 52. Preferably, the straps 22, 24 and fastener receiver 52 are stitched to the hose 10, as seen as 68 in FIG. 2 and 70 in FIG. 1. In the embodiment of FIG. 1, a top locking strap 24 stitched to the top of the hose has a longer length than the lower fastening straps 22 and is sized to extend across the opening and lock the hose in place on the patient's leg.

The foot portion 12, calf portion 14, upper calf portion 15, and thigh portion 16 are constructed of a single-ply hosiery material. Preferably, the hose includes a heel portion 34 and a reinforced toe 32 for extra durability and comfort. The hose is preferably made of a knit construction, such as made on a circular knitting machine. In one preferred embodiment, the hose is knit on a Pandolina circular knitting machine having a reciprocated toe and heel.

Figure 2A:
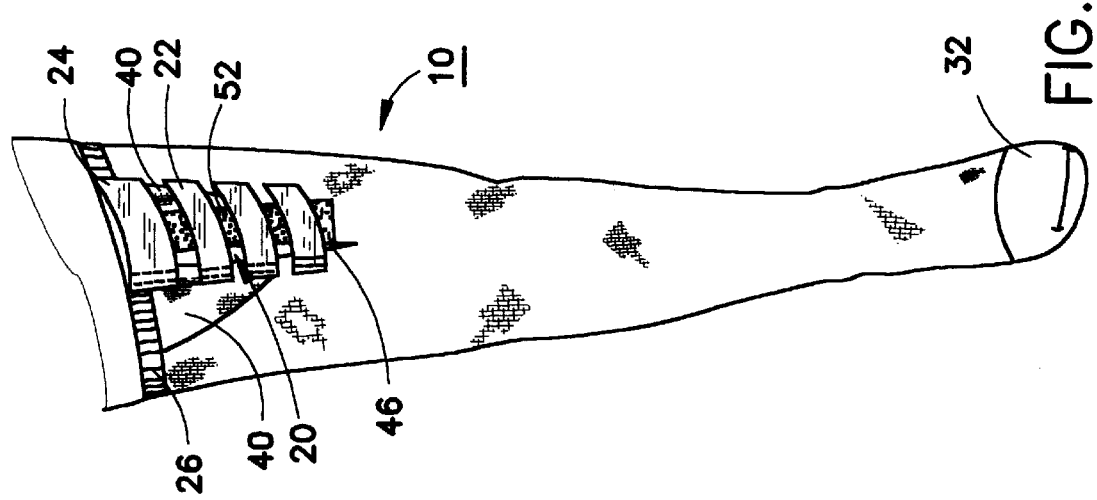
FIG. 2A is a front elevational view of the compression hose having the fasteners in a closed position.

In the embodiment of the invention for application to a leg, as in each of FIGS. 1–3, the hose has an anatomical shape that provides for maximum comfort for the patient and for gradual compression rates along the hose length. The hose provides a compressive force on the leg of the patient starting in the foot area and gradually decreasing upwardly to the upper calf portion 15. The graduated compression assists venous blood flow and reduces blood clotting in the leg. Compression rates just above the patient's ankle are in the range of about 15–20 mm/Hg. Extending upwardly along the length of the hose, the compressive force decreases to the range of about 8–14 mm/Hg at the upper calf portion 15 immediately below the lower extent 46 of the knee opening. In one preferred embodiment, the graduated compression rates of the hose are about 18 mm/Hg just above the patient's ankle and decrease to about 14 mm/Hg immediately below the lower extent 46 of the knee opening. The thigh portion 16 of the hose, including the area from the lower knee opening 46 to the top of the hose, permits compression on the patient's knee and thigh by adjusting the straps 22, 24 to the required amount.

The top edge of the hose worn around the patient's thigh may include an elastic band 26. The elastic band 26 stretches and contracts to form a tight fit to prevent the hose from sliding down the patient's leg. As best seen in FIG. 2, the elastic band 26 extends around only a portion of the top edge of the hose. The remainder of the top edge of the hose includes a knit band 36 included in the panel area 40. In an alternative embodiment, the elastic band 26 may extend around the complete top edge of the hose.

As illustrated in FIG. 3, a panel area 40 positioned on each side of the opening 20 connects to the hose 10 by a seam 42. Preferably, any protruding portion of the seam 42 is positioned on the outside of the hose away from the patient's leg, providing a more comfortable fit. The panel area 40 is preferably constructed of the same knit material as the thigh portion 16 of the hose. The upper edge of the panel includes a knit pattern forming a resilient cuff 36 that stretches and contracts when the patient wears the hose. The elastic band 26 cooperates with the cuff 36 and strap 24 to encircle the thigh to hold the hose in place upon the patient's leg. The tension in the combination of the cuff 36, band 26 and strap 24 can be changed by adjusting the strap 24, with the transmission of the tension through the band 26 and cuff 36.

The lower extent of the opening 46 is located slightly below the patient's knee when the hose is placed upon the patient. The opening 20 extends from the lower extent 46 to the top edge of the hose and is sized to allow access to the patient's knee as well as any bandages or other wound dressings placed on the patient in the knee area. Preferably, the edges of the opening 20 include overlap or serge stitching 72 to prevent fraying or unraveling of the hose.

One side of the opening 20 includes a number of straps 22 fixedly attached to the hose 10 with fastener receivers 52 fixedly positioned upon the opposite opening edge. The fixed attachments can be by sewing or other suitable means. The fastening straps 22 extend over the opening 20 and releasably fasten upon the fastener receivers 52. For instance, the straps 22 may be unfastened and opened to allow access to the bandages on the patient's knee or may be fastened and unfastened to adjust them according to the patient's comfort. In one preferred embodiment, the straps are equipped with hook and loop attachment mechanisms to allow for fastening and unfastening to assist in positioning the straps 22 at any variety of circumferential lengths.

The fastening strap 24 is preferably longer than the lower fastening straps 22 to firmly secure and lock the hose onto the patient. This uppermost strap 24 in combination with the elastic band 26 and panel band 36 act to lock the hose and prevent the hose from sliding down the patient's leg. As with the lower straps 22, the upper strap 24 securely attaches to a fastener receiver 52 on the opposite side of the opening, allowing for numerous attachments and releases of the strap. Preferably, the uppermost strap 24 aligns with the upper edge of the hose as illustrated in FIGS. 2 and 3. The straps 22, 24 provide tension around the patient's knee and thigh area. Preferably, the straps 22, 24 align in close proximity, providing compression along the knee and thigh area. One preferred embodiment includes a total of three or four straps positioned along the opening 20 and spaced about 0.5 inches apart. Thus the amount of compression applied to the knee can be set as desired and account for the fragility of the adjacent healing wound.

The straps 22, 24 may also be arranged such that each alternating strap attaches to the opposite side of the opening and extends across the opening to secure the hose. For example, looking from the front of a patient's leg as illustrated in FIG. 3, the bottom-most strap 60 fixedly attaches on the left side of the opening and extends over to the right side of the opening. The subsequent strap 62 fixedly attaches to the right side of the opening and extends across to fasten and seal on the left side. Straps 64 and 66 likewise alternate sides. This invention contemplates any number of locking arrangements and fastening devices, such as laces, clasps, etc. in place or in combination with the straps. Another embodiment features straps fixedly secured to both sides and connecting over the opening to secure the hose.

In use, the doctor places the hose 10 upon the patient's foot and pulls the hose up the leg such that the toes position in the reinforced toe 32 and the hose extends up to the thigh. The bottom extent of the opening 46 positions directly below the patient's knee and the opening extends upward over the knee. The hose 10 does not disturb bandages or other wound dressings that have been previously placed on the patient's knee. The doctor pulls the straps 22, 24 across the opening and attaches them to the fastener receiver 52. The straps 22, 24 may be pulled open, adjusted, and reclosed to accommodate the patient. The straps 22, 24 fit over the top of the knee area and do not disturb the patient's knee and bandages. The straps further provide compression to the knee and thigh area of the leg to aid in blood flow. The patient or doctor may unfasten the straps 22, 24 to access the knee, change bandages, examine the knee, or various other matters.

The present invention is not limited to the patient's knee and legs, but rather may also be used in other applications. FIG. 4 illustrates the hose placed on the patient's arm such that the opening 20 is positioned over the wrist. The hose includes a hand portion 82 that extends over the hand. The hand portion 82 may be either a mitten-type arrangement as illustrated in FIG. 4 having a thumb covering and a finger covering for all four fingers, a glove arrangement with a separate covering for each finger as illustrated in FIG. 5, or a single covering for both the fingers and thumb. The hose provides for a graduated compression rate along the extremity length.

The opening 20 is positioned over the injured area to provide access and to fit over bandages or other wound dressings. Straps 22 extend across the opening to hold the bandage in position on the patient's arm and can be adjusted to control the amount of compression placed on the injured area. A band 26 positioned at the inner hose edge holds the hose in position on the patient's arm. The hose may extend to the elbow as shown in FIG. 4, or may extend above the elbow.

Another embodiment of the invention is illustrated in FIG. 5 for use on the patient's elbow. The opening 20 is placed over the elbow and straps 22, 24 extend across to hold the hose in position and apply compression to the injured area. The hose provides graduated compression rates from the area of the hand through the lower extent of the opening 46. The hand portion 82 includes a glove-type arrangement with separate compartments for each finger and thumb.

The embodiments shown and described herein have been for the purpose of illustration of the invention. Those of ordinary skill in the art will appreciate that the invention can be carried out in various forms other than those specifically shown. For example, the hose may include an opening over the ankle area and include a foot portion and leg portion. Such variations are deemed to be within the scope of the claims. Also, various combinations and sub-combinations of the features of the invention can be used without going beyond the scope of the invention.

What is claimed is:

1. An apparatus for assisting a patient having an injured extremity in recovery comprising:
   a medical compression hose including
   an extremity covering portion for applying a graduated compression force to the patient's extremity during use, said compression force in the extremity covering portion being greater in the distal area of the extremity and decreasing towards the patient's torso to prevent thrombophlebitis or other circulatory impairment;
   a knee opening located at the proximal end of said hose for positioning over and providing access to the patient's knee; and
   reclosable fasteners on said medical compression hose adjacent to said knee opening for fastening said medical compression hose about the knee, said reclosable fasteners providing closure and compression to the knee.

2. An apparatus as claimed in claim 1, wherein said compression hose is adapted to be applied to the patient's lower leg and knee area, said compression force at the patient's lower leg just above the patient's ankle between about 15 and 20 mm/Hg.

3. An apparatus as claimed in claim 2, wherein said compression force applied to the patient's upper calf immediately below the knee during use is between about 8 and 14 mm/Hg.

4. An apparatus as claimed in claim 1, wherein an edge of said hose includes an elastic band for holding said hose in place on the patient's extremity.

5. An apparatus as claimed in claim 1, wherein said reclosable fasteners are straps attached to a first side of said knee opening, said reclosable fastener straps being of a sufficient length to extend across said knee opening and fasten to a fastener receiver positioned on a second side of said knee opening, said fastener straps being positionable to accommodate a variety of compression rates.

6. An apparatus as claimed in claim 5, wherein said straps and said fastener receiver are stitched to said hose adjacent to said knee opening, said stitching providing for secure attachment of said straps and said fastener receiver.

7. An apparatus as claimed in claim 5, wherein a locking strap nearest the edge of the hose has a longer length than the other straps, said locking strap locks and prevents said hose from sliding along the patient's extremity.

8. An apparatus as claimed in claim 5, wherein said straps are positioned adjacent one another to provide compression to the patient's knee.

9. An apparatus as claimed in claim 5, wherein said hose includes a total of four straps spaced along said knee opening.

10. An apparatus as claimed in claim 1, further having a panel attached to said hose adjacent to said knee opening, said panel providing for said hose to fit around the patient's extremity.

11. An apparatus as claimed in claim 10, wherein a seam connects said panel to said hose, said seam being located on the exterior of said hose, away from the patient's extremity during use.

12. An apparatus as claimed in claim 11, wherein an edge of said hose includes an elastic band, said panel includes an edge, said edge in combination with said elastic band and said straps hold said hose onto the patient's extremity during use.

13. An apparatus for a patient who has an injured extremity comprising:
   a medical compression hose including an extremity covering portion and a knee covering portion, said medical compression hose applying a graduated compression force to the patient's extremity during use, said compression force being greater in the distal area of the extremity and decreasing towards the patient's torso;
   a knee opening in said knee covering portion for positioning over the patient's knee;
   reclosable fasteners attached to said hose on a first side of said knee opening for applying a compression force to the knee of the patient;
   fastener receivers attached to said hose on a second side of said knee opening;
   an elastic band positioned at an edge of said hose; and
   panels attached to said hose adjacent to said knee opening.

14. A method of applying a compression hose to a patient comprising the steps of:
   inserting the patient's extremity into a compression hose;
   pulling the hose onto the patient's extremity such that the hose extends along the extremity;
   applying a graduated compression force via the compression hose to the patient's extremity that is greater in an extremity distal area and decreasing towards the patient's torso;
   positioning a knee opening in said hose over the patient's knee, the knee opening extending a distance less than the length of the hose; and
   releasably fastening straps across the knee opening.

15. The method of claim 14, further comprising unfastening the straps to allow access to the patient's knee.

16. The method of claim 14, wherein when the hose is applied to the patient's leg, the compression rate is between about 15 and 20 mm/Hg at the area above the patient's ankle.

17. The method of claim 16, wherein the compression rate is between about 8 and 14 mm/Hg at the area immediately below the patient's knee.

18. The method of claim 14, further comprising adjusting the compressive force of the hose at the knee by changing the position of the straps on a fastener receiver.

19. A method of applying compression to the extremity of an injured patient comprising the steps of:
   inserting a patient's extremity into a compression hose;
   pulling the hose onto the patient's extremity, thereby applying a graduated compression force to the patient's extremity that is greater in a distal area of the extremity and decreasing towards the patient's torso;
   positioning a knee opening in the hose over the patient's knee;
   releasably fastening straps across said knee opening; and
   adjusting the straps across the knee opening to adjust compressive forces and patient comfort.

20. An apparatus for assisting a knee surgery patient in recovery comprising:
   a medical compression hose including a lower leg covering portion that has graduated compression characteristics and a knee joint covering portion located on the proximal end of the hose to be positioned over and provide access to the patient's knee,
   the knee joint covering portion having knee opening at a front location thereof and reclosable fasteners to permit closure of the knee opening,
   whereby the leg of the patient may be inserted into the hose with the patient's lower leg extending into the lower portion, and dressings on the front of a patient's knee may be applied or changed and the reclosable fasteners may be secured about the dressing to provide compression to leg portions around the front of the knee and prevent thrombophlebitis or other circulatory impairment.

21. An apparatus as claimed in claim 20 wherein the lower leg covering portion is seamless.

* * * * *